United States Patent [19]

Dell et al.

[11] Patent Number: 4,731,384

[45] Date of Patent: Mar. 15, 1988

[54] ETOFENAMATE FORMULATION

[75] Inventors: Hans-Dieter Dell, Bergisch-Gladbach; Reinhold Kraus, Cologne; Detlef Schierstedt, St. Augustin, all of Fed. Rep. of Germany

[73] Assignee: Troponwerke GmbH & Co, KG, Cologne, Fed. Rep. of Germany

[21] Appl. No.: 842,106

[22] Filed: Mar. 20, 1986

Related U.S. Application Data

[63] Continuation-in-part of Ser. No. 622,429, Jun. 20, 1984, abandoned, and a continuation-in-part of Ser. No. 622,424, Jun. 20, 1984, abandoned.

[30] Foreign Application Priority Data

Jul. 1, 1983 [DE] Fed. Rep. of Germany ....... 3323832
Jul. 1, 1983 [DE] Fed. Rep. of Germany ....... 3323833

[51] Int. Cl.$^4$ .................. A61K 31/135; A61K 31/715; A61K 31/695; A61K 31/61
[52] U.S. Cl. ........................................ 514/658; 514/57; 514/63; 514/163; 514/234; 514/356; 514/506; 514/549; 514/552; 514/724; 514/762; 514/825; 514/886; 514/943; 514/965; 424/78; 424/79; 424/80; 424/81; 424/82; 424/83; 424/154

[58] Field of Search ............... 514/658, 825, 886, 969, 514/943, 234, 549, 552, 506, 724, 63, 762, 356, 163, 57; 424/78–83, 154

[56] References Cited

FOREIGN PATENT DOCUMENTS 0043738 1/1982 European Pat. Off. .
0054205 6/1982 European Pat. Off. .
0063870 11/1982 European Pat. Off. .

OTHER PUBLICATIONS

Arzneimittelforschung, 27, (I), Special Edition 6b, p. 1300, (1977).
Rote Liste, 1982, p. 452, Editio Cantor, Aulendorf-/Württ., DE., No. 05448: "Rheumon".
Merck Index 9th ed p. 684–5075, 1976.
Chem Absts. 92:379e, 1980; 97:13809s; 97:138310k; 97:138311; 97; 1982 and 100:6096r, 1984.

*Primary Examiner*—J. R. Brown
*Assistant Examiner*—John W. Rollins
*Attorney, Agent, or Firm*—Sprung Horn Kramer & Woods

[57] ABSTRACT

The invention relates to topical antiinflammatory medicament formulations which also have analgesic activity and contain 2-(2-hydroxyethoxy)-ethyl N-($\alpha,\alpha,\alpha$,-trifluoro-m-tolyl) anthranilate as the active ingredient and an adjuvant which is preferably a triglyceride.

19 Claims, No Drawings

ETOFENAMATE FORMULATION

CROSS-REFERENCES TO RELATED APPLICATIONS

The present application is a continuation-in-part application of application Ser. No. 622,429, filed June 20, 1984, now abandoned and application Ser. No. 622,424, filed June 20, 1984, now abandoned.

BACKGROUND OF THE INVENTION

The present invention relates to an antiinflammatory medicament formulation which has an analgesic action and is to be applied topically, and which contains 2-(2-hydroxyethoxy)-ethyl N-($\alpha,\alpha,\alpha$-trifluoro-m-tolyl)anthranilate, called Etofenamate below, as the essential active compound. Etofenamate has the following structure:

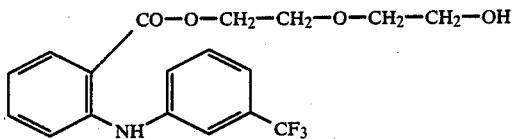

Etofenamate is already known as a non-steroid medicament with a good antiinflammatory action and outstanding tolerance, compare Arzneimittelforschung 27 (I) Special Edition 6 b, 1299–1364, 1977. Etofenamate has hitherto been used in the form of alcohol-containing gels. Because of the alcohol, the gel has a cooling action when applied, and this has not been found pleasant by all patients. Furthermore, such a gel can be applied only to intact skin, and a desirable application in cases of trauma with open wounds is thus not possible. In addition, such a formulation is of only limited suitability for patients with an exceptionally dry skin.

An object of the present invention is thus to overcome the disadvantages described by providing a new formulation which, however, has the antiinflammatory and analgesic action to the same degree as the gel form.

Surprisingly, it has been possible to discover cream and ointment formulations which have the required properties.

The present invention thus relates to cream and ointment formulations containing Etofenamate and an adjuvant.

Etofenamate is a highly viscous oil, only traces of which dissolve in water. In a large number of galenical auxiliaries, it has only inadequate solubility, interactions, such as, for example, hydrolysis, transesterification, esterification and the like, take place, or demixing, phase separation and the like occurs. Although some formulations containing Etofenamate have proved homogeneous and stable, their absorption is inadequate in comparison with the known Etofenamate-containing gel. These disadvantages do not arise in the formulation according to the invention. In the formulation according to the invention, the absorption of Etofenamate by the skin is outstanding.

BACKGROUND OF THE INVENTION

The cream and ointment formulations according to the present invention thus also contain, in addition to Etofenamate, an adjuvant and, if appropriate, agents which give the formulation consistency and/or emulsifiers and other auxiliaries, such as additives which promote circulation or have a warming effect or which have a pleasant odor.

According to the invention, one or more compounds from the groups: triglycerides, and/or esters of monohydric and/or polyhydric alcohols, and/or higher alcohols, are used as the adjuvant.

Adjuvants which are preferably used from the triglyceride group are one or more triglycerides of medium-chain carboxylic acids of $C_6$ to $C_{14}$ chain length in saturated or unsaturated, preferably mono-unsaturated and branched or straight-chain form, particularly preferably, neutral oils, such as, for example, Miglyol 810 ® or Miglyol 812 ® or Viscoleo ®.

Viscoleo ® is understood as meaning a mixture of saturated triglycerides of medium chain length and a fatty acid distribution of 45–60% of caprylic acid, 35–50% of capric acid and 2–10% of lauric acid, and Miglyol ® is understood as meaning a caprylic/capric acid triglyceride.

An adjuvant from the group of esters of monohydric and/or polyhydric alcohols is preferably understood as meaning one or more esters of monohydric and/or polyhydric alcohols of $C_1$–$C_{18}$ (preferably $C_2$ to $C_{18}$) chain length with carboxylic acid components of $C_6$–$C_{18}$ chain length, especially where the alcohols are alkanols or alkenols and the carboxylic acids are alkane or alkene - carboxylic acids, particularly preferably are propylene glycol diesters, ethyl oleate, isopropyl myristate, stearate or palmitate, diisopropyl adipate, diethyl sebacate, oleyl oleate, hexyl laurate and isooctyl stearate, and very particularly preferably diisopropyl adipate and/or isopropyl myristate.

Adjuvants from the group of $C_8$–$C_{20}$ alcohols are used to accomplish the objections of the invention.

An adjuvant from the group of higher alcohols is preferably understood as meaning oleyl alcohol and/or 2-octyl-dodecanol, particularly preferably 2-octyl-dodecanol, by itself.

According to the invention, Etofenamate can be present in the formulations as a mixture with one or more adjuvants of all three groups or of only two groups or only one group.

Starting from these Etofenamate/adjuvant mixtures or solutions, various creams of a liquid to semi-solid consistency can be prepared: 1. Oil-in-water emulsions, 2. Water-in-oil emulsions and 3. Microemulsions.

According to the invention, it is necessary for the cream consisting of the active compound and adjuvant to contain about 2 to about 30% by weight of Etofenamate as the active compound and about 5 to about 80% by weight of adjuvant or adjuvant mixtures as described above.

According to the invention, it is necessary for the ointment consisting of the active compound and adjuvant to contain about 5 to about 40% by weight of Etofenamate as the active compound and about 3 to about 95% by weight of adjuvant or adjuvant mixtures as described above. The mixture particularly preferably contains 5–15% by weight of Etofenamate, and particularly preferably 6–12% by weight.

The formulation can furthermore also contain one or more agents to give it consistency and/or one or more emulsifiers and/or additives which promote circulation or have a warming effect and/or other auxiliaries, such as, for example, substances which have a pleasant odor, and/or also other active compounds.

In many cases, agents which give the formulation consistency and emulsifiers are also identical, and strict separation is thus not possible.

As agents which give the formulation consistency, there may be used one or more of the group of fatty alcohols (especially alkanols or alkenols), of $C_{10}$ to $C_{30}$ chain length, such as for example, stearyl alcohol, hydrocarbons, such as petroleum jelly, paraffins, hard paraffins and waxes, such as beeswax or carnauba wax. It is furthermore also possible to use monoglycerides, diglycerides and triglycerides, such as glycerol monostearate and glycerol distearate, and metal soaps, such as Al stearate, Aerosol ® (silicon dioxide colloid) and polyglycols, such as polyalkylene glycols, such as polyethylene glycols and polypropylene glycols.

The consistency of the aqueous phase of water-containing formulations can be adjusted by means of hydrogel-forming agents, such as Veegum ®, cellulose derivatives (for example methylcellulose, hydroxyethylcellulose or carboxymethylcellulose), carboxyvinyl polymers such as polyacrylates and especially Carbopol 940 ®, 938 ® and 941 ®, alginic acid derivatives, gum arabicum and the like.

As the emulsifier there may be used one or more from the group of ionic or non-ionic water-in-oil and oil-in-water emulsifiers.

Compounds which are preferably used are slats of higher fatty acids and bile acids, such as triethanolamine stearate, alkyl sulphates, such as Na lauryl sulphate, alkylsulphonates, such as Na cetylsulphonate, higher fatty alcohols, such as cetyl alcohol, lauryl alcohol and stearyl alcohol, sterol alcohols, such as cholesterol, fatty acid esters of polyhydric alcohols and polyols, such as ethylene monostearate, glycerol monooleate, sorbitan monolaurate, sorbitan trioleate, polyoxyethylene-(20) sorbitan monolaurate and polyoxyethylene sorbitol hexaoleate, fatty alcohol ethers, such as polyoxyethylene lauryl ether and polyoxyethylene oleyl ether, fatty acid esters of sucrose, such as sucrose distearate, lecithin and derivatives, betaines and sulphobetaines, such as fatty acid amidoalkylbetaine and/or polyoxyethylene/polyoxypropylene polymers, such as pluronics.

Examples of additives which may be used which promote circulation or have a warming effect are benzyl nicotinate, salicylic acid esters, for example methylsalicylate, ethereal oils, capsaicin, capsicum extract or nonylic acid vanillyamide.

The customary pharmacologically acceptable substances can be used as the odor substances, as long as they are compatible with the active compound and adjuvant.

The amount of agents which give the formulation consistency and/or emulsifiers in the formulation, besides the Etofenamate and adjuvant, is up to about 70% by weight, and is preferably 5 to 25% by weight.

Furthermore, the cream formulation also contains up to 85% by weight, preferably 40 to 60% by weight, of water.

Cream formulations containing 2 to 30% by weight of Etofenamate, 5–80% by weight of adjuvant and 40 to 60% by weight of water are particularly preferred.

A preferred cream formulation contains 50 to 100 mg of Etofenamate, 400 to 650 mg of water, 100 to 150 mg of an adjuvant of an emulsifier selected from the group consisting of isopropylmyristate, diisopropyl adipate, Miglyol 810 ® and Miglyol 840 ®, 40 to 60 of Myrj. 59 ®, 0 to 10 mg of Tylose MH 400 (methylcellulose), 30 to 180 mg of Cutina MD ® or Cutina GMS ®, 10 to 50 mg of a citrate buffer, 0 to 15 mg benzyl nicotinate, 0 to 20 mg of cetyl alcohol and 0 to 20 mg of Veegum ®.

Preferred ointment formulations contain up to 250 mg of Etofenamate, 50 to 100 mg of an adjuvant selected from the group consisting of diisopropyl adipate, isopropyl myristate, Miglyol 840 ®, Miglyol 812 ®, oleyl alcohol and diisopropyl stearate, 20 to 60 mg of an emulsifier selected from the group consisting of Cremophor EL ®, Tween 40 ®, Tween 60 ® and Myrj. 59 ®, 0 to 1000 mg of an agent which gives consistency selected from the group consisting of wool wax alcohol ointment DAB 8, Softisan ®, PEG 4000 and Cutina MD ®, 0 to 100 mg of Aerosil ®, 0 to 50 mg of cetyl alcohol, 0 to 500 mg of PEG 400 and 0 to 20 mg of benzyl nicotate.

The formulations, the composition of which can be seen from the examples, are furthermore particularly preferred.

According to the invention, the antiinflammatory, analgesic cream formulations according to the invention are prepared by mixing the Etofenamate, dissolved in a suitable solvent, with any other molten fat/wax emulsifier constituents and then adding, with intensive mixing of the constituents, the aqueous phase, which has been brought to about the same temperature and contains preservatives, buffer and the like. Homogenization is then carried out, for example, by means of a rotor-stator device.

According to the invention, the antinflammatory, analgesic ointment formulations according to the invention are prepared by mixing the Etofenamate, dissolved in a suitable solvent, with any other molten fat/wax emulsifier constituents and then subjecting the mixture to homogenization.

The homogenization temperature depends on the particular formulation and is generally between about 40° and about 60° C.

The Etofenamate formulation according to the invention contains the active compound in stable form and is capable of penetrating the skin without having the entraining function of isopropanol, which is contained in the gel. Comparison studies with Etofenamate gel showed a bioequivalent absorption, which it was possible to demonstrate by an approximately equal absorption rate, timed to the maximum plasma level, maximum plasma level concentration, elimination from the plasma, area under the plasma level curves (AUC) and renal elimination in humans. The present invention may be illustrated in more detail by the following examples.

The Etofenamate formulation according to the invention contains the active compound in stable form and is capable of penetrating the skin without having the entraining function, for example, of isopropanol. Comparison studies with Etofenamate gel showed a bioequivalent absorption, which it was possible to demonstrate by an approximately equal absorption rate, timed to the maximum plasma level, maximum plasma level concentration, elimination from the plasma, area under the plasma level curfves (AUC) and renal elimination in warm-blooded animals.

The equivalence of the absorption is also shown by clinical trials, in which the activity was compared in a double-blind cross-over study against ointment containing 1-(p-chlorobenzoyl)-5-methoxy-2-methylindole-3-acetic acid and against salicylic-containing ointments, and in which the formulation according to the invention had a significantly (p<0.05) better action, for example in Lumbago cases in respect of the Schober distance and the spontaneous, movement and pressure pain, compared with the first comparison product, and proved significantly more effective, for example in cases of acute gonathrosis in respect of the target parameters of joint mobility, joint range and spontaneous and movement pain, compared with the second comparison product.

The present invention may be illustrated in more detail by the following examples.

| Example | 1 | 2 | 3 | 4 | 5 | 6 |
|---|---|---|---|---|---|---|
| Etofenamate (mg) | 100 | 100 | 100 | 100 | 100 | 50 |
| H₂O (mg) | 522.5 | 512.5 | 509 | 522.5 | 613 | 679 |
| Adjuvant (mg) | Isopropyl myristate 100 | Isopropyl myristate 100 | Diisopropyl adipate 100 | Miglyol 840 ® 100 | Diisopropyl adipate 130 | Diisopropyl adipate 110 |
| Emulsifier (mg) | Myrj. 59 ® 50 | Myrj. 59 ® 50 | Myrj. 59 ® 50 | Myrj. 59 ® 50 | Myrj. 59 ® 50 | Myrj. 59 ® 50 |
| Benzyl alcohol (mg) | 15 | 15 | 15 | 15 | 15 | 15 |
| Tylose MH 4000 (mg) | 7.5 | 7.5 | 7.5 | 7.5 | — | — |
| Agent which gives consistency (mg) | Cutina MD ® 175 | Cutina MD ® 175 | Cutina MD ® 175 | Cutina MD ® 175 | Cutina ® GMS 37 | Cutina ® GMS 41 |
| Citrate buffer solution (mg) | 30 | 30 | 30 | 30 | 30 | 30 |
| Benzyl nicotinate | — | 10 | — | — | — | 10 |
| Cetyl alcohol | | | | | 10 | 10 |
| Veegum | | | | | 15 | 15 |

| Example | 7 | 8 | 9 | 10 | 11 |
|---|---|---|---|---|---|
| Etofenamate (mg) | 100 | 100 | 200 | 50 | 200 |
| H₂O (mg) | 603 | 605 | 442 | 582 | 442 |
| Adjuvant (mg) | Diisopropyl adipate 130 | Miglyol 810 ® 130 | Isopropyl-myristate 100 | Isopropyl-myristate 100 | Diisopropyl-adipate 100 |
| Emulsifier (mg) | Myrj. 59 ® 50 | Myrj. 59 ® 50 | Myrj. 59 ® 50 | Myrj. 59 ® 50 | Myrj. 59 ® 50 |
| Benzyl alcohol (mg) | 15 | 15 | 15 | 15 | 15 |
| Tylose MH 4000 (mg) | — | — | 8.0 | 8.0 | 8.0 |
| Agent which gives consistency (mg) | Cutina ® GMS 37 | Cutina ® GMS 45 | Cutina MD ® 155 | Cutina MD ® 165 | Cutina MD ® 155 |
| Citrate buffer solution (mg) | 30 | 30 | 30 | 30 | 30 |
| Benzyl nicotinate | — | — | — | — | — |
| Cetyl alcohol | 10 | 10 | | | |
| Veegum | 15 | 15 | | | |

TABLE

| Example | Etofenamate (mg) | Adjuvant I (mg) | Adjuvant II (mg) | Emulsifier I (mg) | Agent which gives consistency (mg) | Aerosil ® (mg) | Cetyl alcohol | PEG 400 | Benzyl nicotinate |
|---|---|---|---|---|---|---|---|---|---|
| 12 | 50 | Diisopropyl adipate 820 | — | Cremophor EL ® 50 | — | 80 | | | |
| 13 | 200 | Diisopropyl adipate 670 | — | Cremophor EL ® 50 | — | 80 | | | |
| 14 | 50 | Isopropyl myristate 900 | — | Cremophor EL ® 50 | — | — | | | |
| 15 | 200 | Isopropyl myristate 750 | — | Cremophor EL ® 50 | — | — | | | |
| 16 | 50 | Myglyol 840 ® 900 | — | Tween 40 ® 50 | — | — | | | |
| 17 | 200 | Myglyol 670 ® 900 | — | Tween 40 ® 50 | — | 80 | | | |
| 18 | 50 | Miglyol 812 ® 820 | — | Tween 60 ® 50 | — | 80 | | | |
| 19 | 200 | Miglyol 750 ® 820 | — | Tween 60 ® 50 | — | — | | | |

TABLE-continued

| Example | Etofenamate (mg) | Adjuvant I (mg) | Adjuvant II (mg) | Emulsifier I (mg) | Agent which gives consistency (mg) | Aerosil ® (mg) | Cetyl alcohol | PEG 400 | Benzyl nicotinate |
|---|---|---|---|---|---|---|---|---|---|
| 20 | 50 | Oleyl alcohol 450 | Diisopropyl stearate 450 | Cremophor EL ® 50 | — | — | — | — | — |
| 21 | 100 | Isopropyl myristate 770 | — | Tween 40 ® 50 | — | — | 80 | — | — |
| 22 | 100 | Isopropyl myristate 500 | Diisopropyl adipate 260 | Tween 60 ® 50 | — | — | 80 | — | — |
| 23 | 50 | Diisopropyl adipate 100 | — | Myrj 59 ® 50 | Wool wax alcohol ointment DAB 8 780 | — | 20 | — | — |
| 24 | 200 | Diisopropyl adipate 150 | — | Myrj 59 ® 50 | Wool wax alcohol ointment DAB 8 570 | — | 30 | — | — |
| 25 | 50 | Isopropyl myristate 100 | — | Myrj 59 ® 50 | Softisan 378 ® 770 | 30 | — | — | — |
| 26 | 200 | Isopropyl myristate 110 | — | Myrj 59 ® 50 | Softisan 378 ® 615 | 35 | — | — | — |
| 27 | 200 | Isopropyl myristate 120 | — | Myrj 59 ® 50 | PEG 4000 ® 400 | — | — | 230 | — |
| 28 | 50 | Miglyol 810 ® 100 | — | Myrj 59 ® 50 | Wool wax alcohol ointment DAB 8 780 | — | 20 | — | — |
| 29 | 200 | Miglyol 810 ® 150 | — | Myrj 59 ® 50 | Wool wax alcohol ointment DAB 8 545 | 25 | 30 | — | — |
| 30 | 50 | Miglyol 840 ® 100 | — | Myrj 59 ® 50 | Wool wax alcohol ointment DAB 8 780 | — | 20 | — | — |
| 31 | 200 | Miglyol 840 ® 150 | — | Myrj 59 ® 50 | Wool wax alcohol ointment DAB 8 545 | 25 | 30 | — | — |
| 32 | 50 | Isopropyl myristate 520 | — | Myrj 59 ® 50 | Cutina MD ® 380 | — | — | — | — |
| 33 | 200 | Isopropyl myristate 450 | — | Myrj 59 ® 50 | Cutina MD ® 300 | — | — | — | — |
| 34 | 100 | Diisopropyl adipate 840 | — | Myrj 59 ® 50 | — | — | — | — | 10 |

Miglyol 840 ® = propylene glycol diester of caprylic/capric acid
Myrj 59 ® = polyoxyethylene fatty acid ester
Tween 40 ® = polyoxyethylene-20 sorbitan monopalmitate
Tween 60 ® = polyoxyethylene-20 sorbitan monopalmitate
Cremophor E ® = glycerol polyethylene glycol castor oil ester
Cutina MD/GMS ® = mixture of monoglycerides and diglycerides of palmitic acid and stearic acid
Softisan 378 ® = triglycerides of stearic acid, gapric acid and caprylic acid.
Veegum ® = magnesium aluminum silicate
Miglyol 810 ® = triester of caprylic/capric acid glycol It will be appreciated that the instant specification and claims are set forth by way of illustration and not limitation, and that various modifications and changes may be made without departing from the spirit and scope of the present invention.

What is claimed is:

1. A cream or ointment formulation comprising (a) 2-(2-hydroxyethoxy)ethyl N-(α,α,α-trifluorom-tolyol-)anthranilate,
   wherein for said cream (a) is contained in an amount of 2 to 30% by weight and for said ointment, (a) is contained in an amount of 5 to 40% by weight,
   (b) an adjuvant selected from the group consisting of
   (i) a triglyceride of a medium-chain carboxylic acid of $C_6$ to $C_{14}$ chain length in saturated or unsaturated form and branched or straight-chain form,
   (ii) an ester of a monohydric alcohol, a polyhydric alcohol and a mixture thereof, said ester being of a $C_2$ to $C_{18}$ chain length with a carboxylic acid component of a $C_6$ to $C_{18}$ chain length,
   (iii) a $C_8$-$C_{20}$ alcohol and
   (iv) a mixture thereof of (i), (ii) and (iii), wherein for said cream, (b) is contained in an amount of 5 to 8% by weight and for said ointment, (b) is contained in an amount of 3 to 95% by weight, and for said cream, the formulation additionally comprises up to 85 weight % water.

2. A formulation according to claim 1, wherein said triglyceride is selected from the group consisting of a neutral oil; a triester of caprylic/capric acid glycol; and a mixture of a saturated triglyceride of a medium chain length and a fatty acid distribution of 45 to 60% of caprylic acid, 35 to 50% of capric acid and 2 to 10% of lauric acid.

3. A formulation according to claim 1, wherein said ester is selected from the group consisting of a propylene glycol diester, ethyl oleate, isopropyl myristate, stearate, palmitate, diisopropyl adipate, diethyl sebacate, oleyl oleate, hexyl laurate, isooctyl stearate, and a mixture thereof.

4. A formulation according to claim 1, wherein said ester is selected from the group consisting of diisopropyl adipate, isopropyl myristate and a mixture thereof.

5. A formulation according to claim 1, which further comprising an agent which gives consistency to the formulation, said agent being selected from the group consisting of a fatty alcohol of a $C_{10}$ to $C_{30}$ chain length hydrocarbon, monoglyceride, diglyceride and triglyceride.

6. A formulation according to claim 5, wherein said fatty alcohol is selected from the group consisting of an alkanol and an alkenol; said hydrocarbon is selected from the group consisting of petroleum jelly, a paraffi, and a wax, said wax being selected from the group consisting of beeswax and carnauba wax, and a metal soap selected from the group consisting of Al stearate, a silicon dioxide colloid and polyglycol.

7. A formulation according to claim 6, wherein said paraffin is a hard paraffin.

8. A formulation according to claim 1, which further comprises an additive to promote circulation or to have a warming effect, said additive selected from the group consisting of benzyl nicotinate and a salicylic acid ester.

9. A formulation according to claim 1, wherein an aqueous phase is formed and which further comprises a substance which adjusts the consistency of the aqueous phase, said substance selected from the group consisting of a hydrogel-forming agent, a cellulose derivative, a carboxyvinyl polymer, an alginic acid derivative and gum arabicum.

10. A formulation according to claim 9, wherein said cellulose derivative is selected from the group consisting of methylcellulose, hydroxyethyl cellulose and carboxymethyl cellulose.

11. A formulation according to claim 9, wherein said carboxyvinyl polymer is a polyacrylate.

12. A formulation according to claim 1, wherein said 2-(2-hydroxyethoxy)-ethyl N-($\alpha,\alpha,\alpha$-trifluoro-m-tolyl)anthranilate is contained in an amount of 5 to 15% by weight.

13. A formulation according to claim 1, wherein said 2-(2-hydroxyethoxy)-ethyl N-($\alpha,\alpha,\alpha$-trifluoro-m-tolyl)anthranilate is contained in an amount of 6 to 12% by weight.

14. A formulation according to claim 1, which further comprises a compound selected from the group consisting of a salt of a higher fatty acid and a bile acid, a higher fatty alcohol, a fatty acid ester of a polyhydric alcohol and a polyol, a fatty alcohol ether, a fatty acid ester of sucrose, betaine and a polyoxyethylene/polyoxypropylene polymer.

15. A formulation according to claim 14, wherein said salt of a higher fatty acid or a bile acid is selected from the group consisting of a triethanolamine stearate, an alkyl sulphate and an alkylsulphonate; wherein said higher fatty alcohol is selected from the group consisting of cetyl alcohol, lauryl alcohol, stearyl alcohol and sterol alcohol; wherein said ester of a polyhydric alcohol or polyol is selected from the group consisting of ethylene monostearate, glycerol monooleate, sorbitan monolaurate, sorbitan trioleate, polyoxyethylene-(20) sorbitan monolaurate and polyoxyethylene sorbitol hexaoleate; wherein said fatty alcohol ester is selected from the group selected from polyoxyethylene lauryl ether and polyoxyethylene oleyl ether; wherein said fatty acid ester of sucrose is selected from the group consisting of sucrose distearate and lecithin; wherein said betaine is a fatty acid amidoalkyl betaine and wherein said polyoxyethylene/polyoxypropylene polymer is a pluronic polymer.

16. A formulation according to claim 1, wherein said alcohol is selected from the group consisting of olelyl alcohol, 2-octyldodecanol and a mixture thereof.

17. A cream formulation according to claim 1, containing between 40 to 60% by weight water.

18. A cream formulation according to claim 1, containing 50 to 100 mg of the 2(2-hydroxyethoxy)-ethyl N-($\alpha,\alpha,\alpha$-trifluoro-m-tolyl)anthranilate, 400 to 650 mg of water, 100 to 150 mg of said adjuvant selected from the group consisting of isopropylmyristate, diisopropyl adipate, a propylene glycol diester of caprylic/capric acid, 40 to 60 mg of a polyoxyethylene fatty acid ester, 0 to 10 mg of methylcellulose, 30 to 180 mg of a mixture of a monoglyceride and a diglyceride of palmitic acid and stearic acid, 10 to 50 mg of a citrate buffer, 0 to 15 mg benzyl nicotinate, 0 to 20 mg of cetyl alcohol and 0 to 20 mg of magnesium aluminum silicate.

19. An ointment formulation according to claim 1, containing up to 250 mg of 2(2-hydroxyethoxy)-ethyl N-($\alpha,\alpha,\alpha$-trifluoro-m-tolyl)anthranilate, 50 to 1000 mg of an adjuvant selected from the group consisting of diisopropyl adipate, isopropyl myristate, propylene glycol diester of caprylic capric acid, oleyl alcohol and diisopropyl stearate, 20 to 60 mg of an emulsifier selected from the group consisting of glycerol polyethylene glycol castor oil ester, polyoxyethylene-20 sorbitan monopalmitate and polyoxyethylene fatty acid ester, 0 to 1000 mg of an agent which gives consistency selected from the group consisting of wool wax alcohol, a triglyceride of stearic acid, capric acid and caprylic acid, PEG 4000 and a mixture of a monoglyceride and a diglyceride of palmitic acid or stearic acid, 0 to 100 mg of a silicon dioxide colloid, 0 to 50 mg of cetyl alcohol, 0 to 500 mg PEG 400 and 0 to 20 mg of benzyl nicotinate.

* * * * *